United States Patent
Bacher et al.

(10) Patent No.: US 9,757,102 B2
(45) Date of Patent: Sep. 12, 2017

(54) MICRO-INVASIVE MEDICAL INSTRUMENT

(71) Applicant: Karl Storz GmbH & Co. KG, Tuttlingen (DE)

(72) Inventors: Uwe Bacher, Tuttlingen (DE); Daniel Kaercher, Radolfzell (DE); Robin Merz, Furtwangen (DE); Sven Schneider, Tuttlingen (DE); Jochen Stefan, Wald (DE)

(73) Assignee: Karl Storz GmbH & Co. KG, Tuttlingen (DE)

( * ) Notice: Subject to any disclaimer, the term of this patent is extended or adjusted under 35 U.S.C. 154(b) by 55 days.

(21) Appl. No.: 13/865,586

(22) Filed: Apr. 18, 2013

(65) Prior Publication Data

US 2013/0304063 A1 Nov. 14, 2013

(30) Foreign Application Priority Data

Apr. 18, 2012 (DE) .......................... 10 2012 007 648

(51) Int. Cl.
 *A61B 18/12* (2006.01)
 *A61B 17/00* (2006.01)
 (Continued)

(52) U.S. Cl.
 CPC ........ *A61B 17/00234* (2013.01); *A61B 17/29* (2013.01); *A61B 17/295* (2013.01);
 (Continued)

(58) Field of Classification Search
 CPC ............ A61B 18/1402; A61B 18/1442; A61B 18/1445; A61B 18/1447; A61B 17/00234; A61B 17/29; A61B 17/295; A61B 2018/145; A61B 2018/1452; A61B 2018/1455; A61B 2018/1457;
 (Continued)

(56) References Cited

U.S. PATENT DOCUMENTS 5,358,508 A * 10/1994 Cobb ...................... A61B 17/29
 606/170
5,374,277 A * 12/1994 Hassler .................. A61B 17/29
 606/170

(Continued)

FOREIGN PATENT DOCUMENTS

DE 19850068 C1 6/2000
EP 1774914 A1 4/2007
 (Continued)

*Primary Examiner* — Daniel Fowler
(74) *Attorney, Agent, or Firm* — Whitmyer IP Group LLC

(57) ABSTRACT

A medical instrument includes an outer shaft, a manipulation device at the proximal end of the outer shaft, a tool at the distal end of the outer shaft, with a first effecting device for a first function and a second effecting device for a second function, a first transmission device in the outer shaft for transmitting at least either a force or a torque for controlling the first effecting device, and a second transmission device in the outer shaft for transmitting at least either a force or a torque for controlling the second effecting device. The outer shaft is at least either curved or able to be curved or has a pivot joint. The first transmission device and the second transmission device are each designed to be flexible at least in sections.

19 Claims, 4 Drawing Sheets

(51) Int. Cl.
*A61B 17/29* (2006.01)
*A61B 17/295* (2006.01)
*A61B 18/00* (2006.01)
*A61B 18/14* (2006.01)

(52) U.S. Cl.
CPC ...... *A61B 18/1482* (2013.01); *A61B 18/1492* (2013.01); *A61B 18/1445* (2013.01); *A61B 2017/003* (2013.01); *A61B 2017/00473* (2013.01); *A61B 2017/2901* (2013.01); *A61B 2017/294* (2013.01); *A61B 2017/2927* (2013.01); *A61B 2017/2929* (2013.01); *A61B 2018/00607* (2013.01); *A61B 2018/1455* (2013.01)

(58) Field of Classification Search
CPC .............. A61B 19/22; A61B 2017/003; A61B 2017/00473; A61B 2017/2901; A61B 2017/2927; A61B 2017/2929; A61B 2017/294
USPC .......................................................... 606/48
See application file for complete search history.

(56) References Cited

U.S. PATENT DOCUMENTS

| | | | |
|---|---|---|---|
| 5,540,375 A | 7/1996 | Bolanos et al. | |
| 5,611,808 A * | 3/1997 | Hossain | A61B 18/1442 606/167 |
| 5,665,100 A * | 9/1997 | Yoon | A61F 6/206 606/139 |
| 5,690,269 A | 11/1997 | Bolanos et al. | |
| 5,800,449 A * | 9/1998 | Wales | A61B 18/1447 606/170 |
| 6,126,359 A * | 10/2000 | Dittrich | A61B 17/29 403/325 |
| 6,142,957 A | 11/2000 | Diamond et al. | |
| 6,458,130 B1 * | 10/2002 | Frazier | A61B 18/1445 606/207 |
| 6,773,434 B2 * | 8/2004 | Ciarrocca | A61B 18/1445 606/170 |
| 7,384,420 B2 * | 6/2008 | Dycus | A61B 18/1445 606/50 |
| 8,702,740 B2 * | 4/2014 | Oberlaender et al. | 606/184 |
| 2002/0099372 A1 * | 7/2002 | Schulze et al. | 606/51 |
| 2002/0161281 A1 * | 10/2002 | Jaffe | A61B 1/0008 600/114 |
| 2005/0222611 A1 * | 10/2005 | Weitkamp | 606/205 |
| 2007/0142833 A1 * | 6/2007 | Dycus | A61B 18/1445 606/51 |
| 2010/0094289 A1 * | 4/2010 | Taylor et al. | 606/52 |
| 2011/0009863 A1 * | 1/2011 | Marczyk | A61B 18/1445 606/51 |
| 2011/0251613 A1 | 10/2011 | Guerra et al. | |
| 2011/0276048 A1 | 11/2011 | Kerr et al. | |
| 2011/0295313 A1 * | 12/2011 | Kerr | A61B 18/1445 606/205 |
| 2012/0080500 A1 | 4/2012 | Morgan et al. | |

FOREIGN PATENT DOCUMENTS

| | | |
|---|---|---|
| EP | 2366338 A2 | 9/2011 |
| WO | 9508945 A2 | 4/1995 |

* cited by examiner

MICRO-INVASIVE MEDICAL INSTRUMENT

FIELD OF THE INVENTION

The present invention relates to a medical instrument for micro-invasive surgical applications.

BACKGROUND OF THE INVENTION

The expectations placed on medical instruments for micro-invasive interventions are constantly increasing. Medical instruments having a tool with a grasping or cutting function at the distal end, where the tool is rotatable about the longitudinal axis of the shaft, are already widely available in many forms. The grasping or cutting function and the rotation of the tool can be controlled, for example, by a single transmission rod, which transmits longitudinal forces and torques. Moreover, in recent times, the shaft can be angled proximally of the tool, and, in order to control this angle, a second transmission element can be provided in the shaft of the medical instrument, for example a second transmission rod.

SUMMARY OF THE INVENTION

An object of the present invention is to make available an improved medical instrument, in particular a medical instrument that is more versatile and can be better adapted to different tasks and uses.

This object is achieved by the subject matter of the independent claims.

Developments are set forth in the dependent claims.

A medical instrument comprises an outer shaft, a manipulation device at the proximal end of the outer shaft, a tool at the distal end of the outer shaft, with a first effecting device for a first function and a second effecting device for a second function, a first transmission device in the outer shaft for transmitting at least either a force or a torque for controlling the first effecting device, and a second transmission device in the outer shaft for transmitting at least either a force or a torque for controlling the second effecting device, wherein the outer shaft is at least either curved or able to be curved or has a pivot joint, and wherein the first transmission device and the second transmission device are each designed to be flexible at least in sections.

The medical instrument is in particular a medical instrument for micro-invasive surgical applications. The second effecting device is designed for a second function that is different than the first function and that can be controlled independently of the first function. For this purpose, the first effecting device can be controlled by means of the first transmission device, and the second effecting device can be controlled independently thereof by means of the second transmission device.

In particular, the first effecting device and the second effecting device have no component parts in common. The second effecting device can be designed as a fully independent structural part that can be separated from the first effecting device without destruction. The first effecting device is in particular designed to be able to perform its intended function and action even in the absence of the cutting device.

The first effecting device comprises in particular several jaw parts, of which at least one is pivotable, for grasping or squeezing tissue. The second effecting device comprises in particular a scalpel or a knife with a cutting edge for cutting through tissue, in particular for cutting through tissue that has been grasped, squeezed and obliterated beforehand by means of the first effecting device.

The outer shaft is curved in particular, in order to permit or simplify use in single-port surgery, in which several medical instruments are introduced through a single opening or a single access point into a hollow space. Curvability of the outer shaft signifies a reversible, destruction-free, elastic and/or plastic deformability of the outer shaft. Alternatively or in addition to a curvature or a curvability of the outer shaft, it is possible to provide a pivot joint, which is substantially perpendicular to the longitudinal axis of the outer shaft. In the case of a curvature of the outer shaft, the pivot axis of the pivot joint is in particular perpendicular to the local longitudinal axis of the outer shaft near the pivot joint.

Particularly for single-port surgery, a (for example substantially helically) curved outer shaft with a pivot joint near its distal end can considerably improve the application possibilities of the outer shaft.

The first transmission device and the second transmission device are each completely flexible or have one or more flexible sections. In order to transmit longitudinal forces and/or torques, the transmission devices are each rigid in the longitudinal direction and/or torsionally rigid. The flexibility of the first transmission device and of the second transmission device is based in each case on an elastic or reversible plastic deformability, in particular on bending elasticity, and/or on one or more pivot joints in the corresponding transmission device.

A medical instrument with the features described here can permit particularly versatile or universal application. On account of the curvature or the curvability of the outer shaft and/or by means of the pivot joint, the tool with the two effecting devices for two different functions can be optimally positioned with respect to the tissue in a great many situations, the tissue being grasped, squeezed, obliterated and cut through, for example. Medical personnel no longer have to decide, or have to decide much less often, as to which medical instrument to choose from a large number of alternative instruments (with different functions and a different arrangement of a tool with a effecting device) and then use. A greater number of different steps can be performed with a single medical instrument, with the result that, during a micro-invasive surgical intervention, the medical instrument being used has to be exchanged much less often. It is possible in this way to reduce the time period required for a specific micro-invasive surgical intervention, to lessen the burden placed on the patient and on the medical personnel, and to reduce costs. Cost reductions are achieved by the fact that the versatility of the individual medical instrument means that a smaller number of instruments have to be kept in stock.

In a medical instrument as described here, the tool and the outer shaft have, in particular, coupling devices by which the tool is mechanically connected in a releasable manner to the distal end of the outer shaft.

The coupling devices are in particular designed to form a mechanical connection that can be released without destruction and that is reversible. The coupling devices comprise, in particular, bayonet coupling devices, screw threads or other devices for the form-fit or force-fit releasable mechanical connection.

The releasability of the connection between tool and outer shaft can make it easier to clean the medical instrument after use and to prepare it for a further use. Moreover, the releasable mechanical connection between tool and outer shaft can make it easier to exchange the tool or the outer shaft in the event of a defect. Moreover, several different tools with different features and/or several different outer shafts with different features can be kept in stock and can be used in the manner of a modular system.

In a medical instrument as described here, outer shaft and manipulation device have, in particular, coupling devices for releasable mechanical connection of the proximal end of the outer shaft to the manipulation device.

The coupling devices are in particular designed for destruction-free and reversibly releasable connection of the outer shaft and manipulation device.

In a medical instrument as described here, the first transmission device and the second transmission device are in particular arranged coaxially in the outer shaft.

A coaxial arrangement of the first transmission device and of the second transmission device in the outer shaft is obtained when the first transmission device and the second transmission device are arranged coaxially to each other in the outer shaft. Moreover, the first transmission device and the second transmission device can be arranged coaxially with respect to the outer shaft. A coaxial arrangement can in particular facilitate a rotatability of the outer shaft relative to the manipulation device and/or a rotatability of the tool relative to the outer shaft and/or a rotatability of a pivot joint relative to a proximal section of the outer shaft.

In a medical instrument as described here, the first transmission device and the second transmission device are, in particular, arranged alongside each other in the outer shaft.

An arrangement of the first transmission device and of the second transmission device alongside each other may be advantageous in respect of the required installation space, particularly in respect of the necessary cross sections. In particular, a smaller cross-sectional surface of the outer shaft can be achieved than in the case of a coaxial arrangement.

A medical instrument with a pivot joint, as described here, also comprises, in particular, a third transmission device, of which the distal end is coupled to the pivot joint, in order to control the pivot joint.

The third transmission device is coupled directly or indirectly to the pivot joint, in particular by means of a linking rod or by means of slide surfaces, in such a way that a longitudinal translation of the third transmission device parallel to the outer shaft is associated with a pivoting of the tool about the pivot axis of the pivot joint. The third transmission device is designed to be elastic, particularly in the case of a curved or curvable outer shaft.

A medical instrument as described here also comprises, in particular, a rotation joint located proximally of the pivot joint, for rotating the pivot joint relative to the proximal end of the outer shaft, wherein the third transmission device is further designed to control the rotation joint.

The rotation joint is in particular arranged immediately proximally of the pivot joint, the distance between the pivot axis of the pivot joint and the rotation joint being only a few (at most 5 or 10) external diameters of the outer shaft. The rotation axis of the rotation joint is in particular parallel to the longitudinal axis of the outer shaft, and, in the case of a curvature or a curvability of the outer shaft, is parallel to the local longitudinal axis of the outer shaft near the rotation joint. A rotation of the pivot joint about the rotation axis of the rotation joint is also associated with a rotation of the pivot axis of the pivot joint.

In a medical instrument as described here, the third transmission device is arranged, in particular, coaxially in the outer shaft.

In particular, the third transmission device has the form of a tube or a hose and is arranged in a substantially annular space between the outer shaft, on the one hand, and the first transmission device and the second transmission device, on the other hand.

In a medical instrument as described here, the first effecting device is designed in particular as a bipolar electrosurgical instrument with mutually electrically insulated electrodes, wherein one of the mutually electrically insulated electrodes is connected electrically conductively to the outer shaft and to the first transmission device.

The mutually electrically insulated electrodes are in particular each formed by a respective jaw part of the first effecting device or are provided on a respective jaw part of the first effecting device. The mutually electrically insulated electrodes can be connected via the outer shaft or via the first transmission device to an electrical high-frequency output source and to the poles thereof.

In particular, in a medical instrument as described here, the second transmission device is mechanically connected to the tool in a releasable manner by means of a bayonet coupling, and a locking device is provided on the second transmission device for the purpose of coupling the second transmission device to the first transmission device or to the outer shaft or to a third transmission device, in such a way that the second transmission device is not rotatable relative to the first transmission device or relative to the outer shaft or relative to the third transmission device.

The second transmission device is connected to the second effecting device, in particular directly, by means of the bayonet coupling. The locking device serves to directly lock the bayonet coupling by suppressing the rotation of the second transmission device relative to the tool, in particular relative to the second effecting device, which rotation is necessary for the release of the bayonet coupling. The locking device can be arranged near the bayonet coupling and thus near the distal end of the second transmission device. With sufficient torsional rigidity of the second transmission device and of the outer shaft, the first transmission device or the third transmission device, it is alternatively possible to provide the locking device at any other desired location on the second transmission device, for example at the proximal end thereof.

The described combination of a bayonet coupling with a locking device permits releasability of the mechanical connection between tool and second transmission device in a way that requires little installation space. Since the locking device can be arranged at a distance from the bayonet coupling, for example at the proximal end of the medical instrument, installation space can be saved in particular at the distal end of the medical instrument.

A medical instrument as described here also comprises, in particular, a rotation joint arranged proximally of the tool, for rotating the tool relative to the outer shaft.

The rotation joint arranged proximally of the tool can be connected non-releasably to the tool. In the case of a pivot joint, the rotation joint is provided distally of the pivot joint, or between tool and pivot joint. The rotation joint arranged proximally of the tool can permit an optimal alignment or orientation of the tool.

BRIEF DESCRIPTION OF THE DRAWINGS

Embodiments are explained in more detail below with reference to the attached figures, in which.

DETAILED DESCRIPTION OF THE INVENTION

Figure 1:
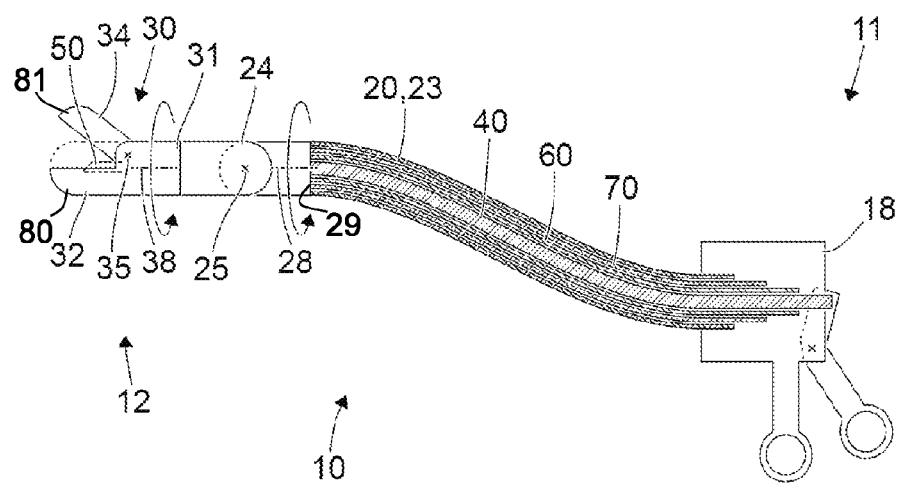
FIG. 1 shows a schematic view of a medical instrument.

FIG. 1 shows a schematic view of a medical instrument 10 with a proximal end 11 and a distal end 12. The medical instrument 10 has, at the proximal end 11, a manipulation device 18 with a plurality of movable grip parts and other actuating devices. A curved outer shaft 20 extends from the manipulation device 18 at the proximal end 11 to a grasping device 30 and a cutting device 50 at the distal end 12 of the medical instrument 10.

Whereas in FIG. 1 the manipulation device 18 is indicated only by its contours and the grasping device 30 and the cutting device 50 are shown in a side view, a substantially tubular section 23 of the outer shaft 20 is shown in longitudinal section. The tubular section 23 contains, in a coaxial arrangement, a transmission rod 40, an internal inner shaft 60 and an external inner shaft 70. The internal inner shaft 60 and the external inner shaft 70 are each tubular or hose-shaped. The transmission rod 40, the internal inner shaft 60 and the external inner shaft 70 are each flexurally elastic, stiff in respect of longitudinal forces and torsionally rigid. The internal inner shaft 60 is arranged in an annular space between the transmission rod 40 and the external inner shaft 70. The external inner shaft 70 is arranged in an annular space between the internal inner shaft 60 and the tubular section 23 of the outer shaft 20.

Arranged immediately proximally of the grasping device 30, a pivot joint 24 is provided which is connected mechanically to the tubular section 23 of the outer shaft 20, either releasably or non-releasably, and in particular forms a component part of the outer shaft 20. The pivot joint 24 permits a pivoting of the grasping device 30 and of the cutting device 50 about a pivot axis 25 perpendicular to the plane of the drawing of FIG. 1. The pivot joint 24 and the pivot axis 25 are rotatable, relative to the curved, tubular section 23 of the outer shaft 20, about a rotation axis 28 in the plane of the drawing in FIG. 1. The rotation axis 28 is defined by a rotation joint 29, shown schematically in FIG. 1.

The proximal end 31 of the grasping device 30 is mechanically connected to the pivot joint 24 in a releasable manner. A stationary jaw part 32 and a pivotable jaw part 34, which is pivotable about a pivot axis 35 perpendicular to the plane of the drawing of FIG. 1, form the distal end of the grasping device 30. The solid line shows the pivotable jaw part 34 in an open position, spaced apart from the stationary jaw part 32, and the broken line shows it in a closed position, bearing on the stationary jaw part 32. Together with the pivot axis 35 and the cutting device 50, the grasping device 30 is rotatable about the longitudinal axis 38 of the grasping device 30 relative to the pivot joint 24.

In the embodiment shown in FIG. 1, the stationary jaw part 32 and the pivotable jaw part 34 are configured as a bipolar electrosurgical instrument with mutually electrically insulated electrodes 80, 81, shown schematically.

Figure 2:
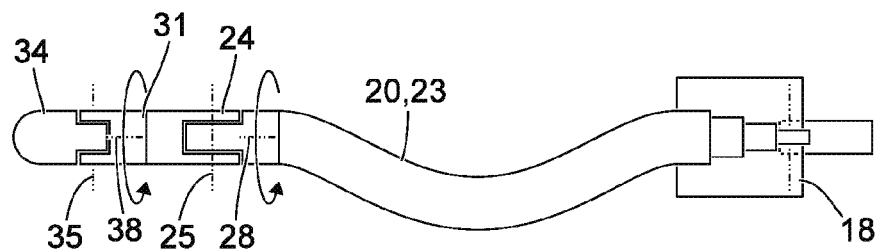
FIG. 2 shows a further schematic view of the medical instrument from FIG. 1.

FIG. 2 shows a further schematic view of the medical instrument 10 from FIG. 1. The plane of the drawing of FIG. 2 is perpendicular to the plane of the drawing of FIG. 1 and parallel to the pivot axis 25 of the pivot joint 24 and to the rotation axis 28 about which the pivot joint 24 is rotatable relative to the tubular section 23 of the outer shaft 20. In contrast to FIG. 1, the outer shaft 20 in FIG. 2 is shown exclusively in an external and side view.

Figure 3:
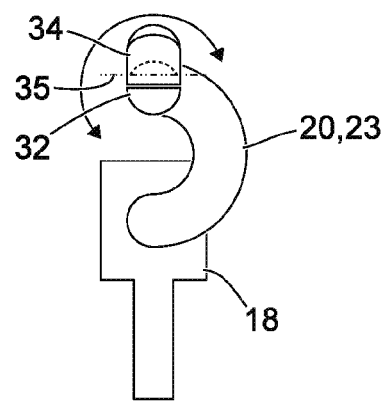
FIG. 3 shows a further schematic view of the medical instrument from FIGS. 1 and 2.

FIG. 3 shows a further schematic view of the medical instrument from FIGS. 1 and 2. The plane of the drawing of FIG. 3 is perpendicular to the plane of the drawing of FIG. 1, perpendicular to the plane of the drawing of FIG. 2, perpendicular to the longitudinal axis 38 of the grasping device 30 (cf. FIG. 2), perpendicular to the rotation axis 28 about which the pivot joint 24 is rotatable relative to the tubular section 23 of the outer shaft 20, parallel to the pivot axis 25 of the pivot joint 24 and parallel to the pivot axis 35 of the pivotable jaw part 34.

Comparing FIGS. 1 to 3, it will be seen that the outer shaft 20 has a spatial curvature, i.e. not a planar curvature, and in particular has a configuration similar to a screw or a helix.

Figure 4:
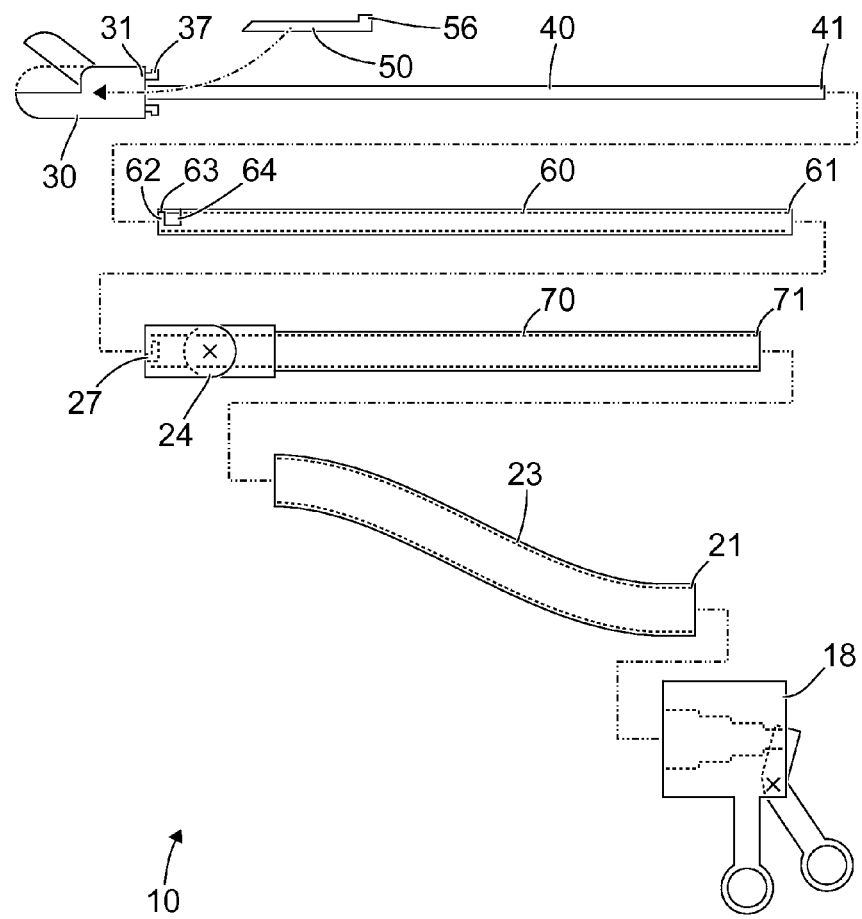
FIG. 4 shows a further schematic view of the medical instrument from FIGS. 1 to 3.

FIG. 4 shows a further schematic view of the medical instrument from FIGS. 1 to 3. The plane of the drawing of FIG. 4 corresponds to the plane of the drawing of FIG. 1. The view in FIG. 4 differs from the views in FIGS. 1 to 3 in that component parts into which the medical instrument 10 can be dismantled without destruction, i.e. reversibly, by medical personnel without using tools, are shown separately. The flexurally elastic transmission rod 40, the flexurally elastic internal inner shaft 60 and the flexurally elastic external inner shaft 70 are each shown in rectilinear form. Dot-and-dash lines indicate how the component parts of the medical instrument are to be assembled.

The flexurally elastic, torsionally rigid transmission rod 40, which is stiff with respect to longitudinal forces, is mechanically connected to the grasping device 30. As is explained in detail below with reference to FIG. 5, the distal end of the transmission rod 40 is mechanically coupled and electrically conductively connected to the pivotable jaw part 34 and is electrically insulated from the stationary jaw part 32 and from bayonet claws or catches 37 at the proximal end 31 of the grasping device 30. As is likewise explained below with reference to FIGS. 5 to 7, the grasping device 50 can be inserted from the proximal direction into a channel in the transmission device 40 and into the grasping device 30.

The tubular or hose-shaped internal inner shaft 60 has a lumen whose cross section is adapted to the cross section of the transmission rod 40, such that the transmission rod 40 is guided with minimal play and minimal friction in the internal inner shaft 60. At the distal end 62, the internal inner shaft 60 has an L-shaped slit with an axial section 63 and a circumferential section 64. The L-shaped slit 63, 64, a projection 56 on the cutting device 50, and the function thereof, are likewise explained below with reference to FIGS. 5 to 7.

The external inner shaft 70 is mechanically connected to the pivot joint 24. In particular, the distal end of the external inner shaft 70 is coupled to the pivot joint 24 in such a way that an axial translation movement of the external inner shaft 70 is associated with a pivoting movement of the distal part of the pivot joint 24 about the pivot axis 25 relative to the proximal part of the pivot joint 24. At the distal end of the pivot joint 24, L-shaped grooves 27 are formed which correspond to the catches 37 at the proximal end 31 of the grasping device 30, for releasable mechanical connection of the tool 30 to the pivot joint 24. The proximal end of the pivot joint 24 can be mechanically connected in a releasable manner to the distal end of the tubular section 23 of the outer shaft 20 by means of devices not shown in FIG. 4. In particular, bayonet coupling devices are provided at the proximal end of the pivot joint 24 and at the distal end of the tubular section 23 of the outer shaft 20.

The external inner shaft 70 is substantially tubular or hose-shaped. The cross section of the lumen of the external inner shaft 70 is adapted to the cross section of the internal inner shaft 60 in such a way that the internal inner shaft 60 is guided and movable in the external inner shaft 70 with minimal play and minimal friction. The cross section of the lumen of the tubular section 23 of the outer shaft 20 is adapted to the cross section of the external inner shaft 70 in such a way that the external inner shaft 70 is guided and movable in the tubular section 23 of the outer shaft 20 with minimal play and minimal friction.

The proximal end 21 of the outer shaft 20, or of the tubular section 23 of the outer shaft 20, can be locked with a form fit in a corresponding recess in the manipulation device 18 by means of a locking device not shown in FIGS. 1 to 4. In the arrangement shown in FIG. 1, the proximal end 41 of the transmission rod 40, the proximal end 61 of the internal inner shaft 60 and the proximal end 71 of the external inner shaft 70 are mechanically coupled to actuating devices on the manipulation device 18 by way of devices not shown in FIGS. 1 to 4.

In particular, the proximal end 41 of the transmission rod 40 is coupled to a pivotable grip part of the manipulation device 18 in such a way that the transmission rod 40 is displaceable in its longitudinal direction, in order to pivot the pivotable jaw part 34 between the open position, shown by solid lines in FIGS. 1, 3 and 4, and the closed position, shown by broken lines in FIGS. 1, 3 and 4. Moreover, the transmission rod 40 is coupled to a further actuating device, for example a rotary wheel, in such a way that the transmission rod 40 is rotatable about its longitudinal axis, in order to rotate the grasping device 30 about its longitudinal axis 38 together with the cutting device 50.

Moreover, the proximal end 61 of the internal inner shaft 60 is coupled to a further actuating device of the manipulation device 18 in such a way that the internal inner shaft 60 can be displaced axially, i.e. in its longitudinal direction, in order to move the cutting device 50 parallel to the longitudinal axis 38 of the grasping device 30. Moreover, the proximal end 71 of the external inner shaft 70 is mechanically coupled to a further actuating device of the manipulation device 18 in such a way that the external inner shaft 70 can be displaced axially, i.e. in the longitudinal direction, in order to pivot the grasping device 30 and the cutting device 50, together with the distal part of the pivot joint 24, about the pivot axis 25. Moreover, the proximal end 71 of the external inner shaft 70 is mechanically coupled to a further actuating device of the manipulation device 18 in such a way that the external inner shaft can be rotated about its longitudinal axis, in order to rotate the pivot joint 24, together with the pivot axis 25, about the rotation axis 28 relative to the distal end of the tubular section 23 of the outer shaft 20.

Figure 5:
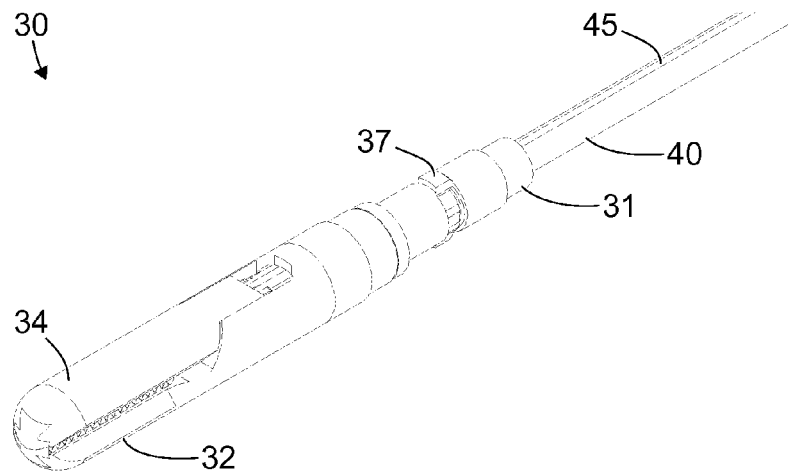
FIG. 5 shows a schematic axonometric view of a grasping device for a medical instrument.

FIG. 5 shows a schematic axonometric view of the grasping device 30, which is provided and designed to form a medical instrument, as is explained above with reference to FIGS. 1 to 4. The grasping device 30 has a proximal end 31 and two jaw parts 32, 34, which form the distal end of the grasping device 30. Near the proximal end 31, the grasping device 30 has two symmetrically arranged bayonet claws or catches 37, of which one is arranged on a side facing away from the viewer and is therefore largely concealed. The grasping device 30 shown in FIG. 5 differs from what has been explained above with reference to FIGS. 1 to 4 in terms of a slightly different arrangement of the catches 37. Otherwise, the grasping device 30 shown in FIG. 5 corresponds substantially to the grasping device of the medical instrument explained above with reference to FIGS. 1 to 4.

The grasping device 30 is mechanically connected to the transmission rod 40. The transmission rod 40 is movable, within a predetermined range, relative to the grasping device 30, in particular relative to the proximal end 31 and to the stationary jaw part 32, in the axial direction, i.e. parallel to the longitudinal axis of the transmission rod 40 and to the longitudinal axis 38 of the grasping device 30 (cf. FIGS. 1 and 2). The distal end of the transmission rod 40 is arranged inside the grasping device 30 and is therefore not visible in FIG. 5, and it is coupled to the pivotable jaw part 34 in such a way that an axial movement of the transmission rod 40 is associated with a pivoting movement of the pivotable jaw part 34.

A groove 45, which in particular has a narrow and deep rectangular cross section, is provided in the transmission rod 40. At its distal end, not visible in FIG. 5, the groove 45 in the transmission rod 40 is continued by a channel of corresponding cross section which extends between the jaw parts 32, 34 to almost the distal ends of the latter.

Parts of the grasping device 30, in particular the catches 37 and the transmission rod 40, are made of stainless steel or another metal. The catches 37 and the transmission rod 40 are electrically insulated from each other. The jaw parts 32, 34 have metallic and therefore electrically conductive grasping surfaces, which are electrically insulated from each other when they are not bearing on each other as shown in FIG. 5. The catches 37 and the transmission rod 40 are each electrically conductively connected to the grasping surface of a jaw part 32, 34. In particular, the catches 37 are electrically conductively connected to the grasping surface of the stationary jaw part 32, and the transmission rod 40 is electrically conductively connected to the grasping surface of the pivotable jaw part 34.

Figure 6:
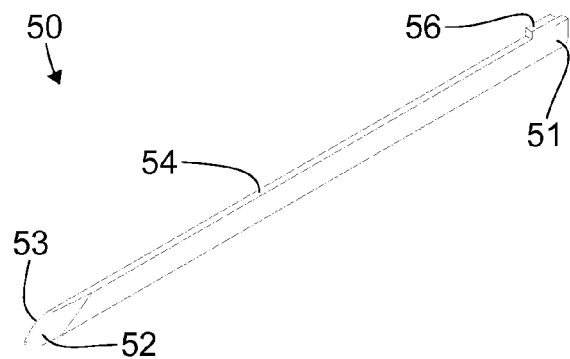
FIG. 6 shows a schematic axonometric view of a cutting device.

FIG. 6 shows a schematic axonometric view of the cutting device 50 with a proximal end 51 and a distal end 52. At the distal end 52, the cutting device 50 has a cutting edge 53. At the proximal end, the cutting device 50 has a projection 56. Between the proximal end 51 and the distal end 52, the cutting device comprises a rod-shaped area 54, which has substantially the configuration of a strip-shaped plate or of a rod with a rectangular cross section.

Between the projection 56 at the proximal end 51 and the cutting edge 53 at the distal end 52, the cross section of the cutting device 50 corresponds substantially to the cross section of the groove 45 in the transmission rod 40 (cf. FIG. 5), such that the cutting device 50 is received completely, except for the projection 56, by the groove 45 in the transmission device 40 and is guided in the latter with minimal play and minimal friction and can be moved in the longitudinal direction of the transmission rod 40 and of the cutting device 50. The projection 56 is provided to protrude from the groove 45 in the transmission rod 40.

Figure 7:
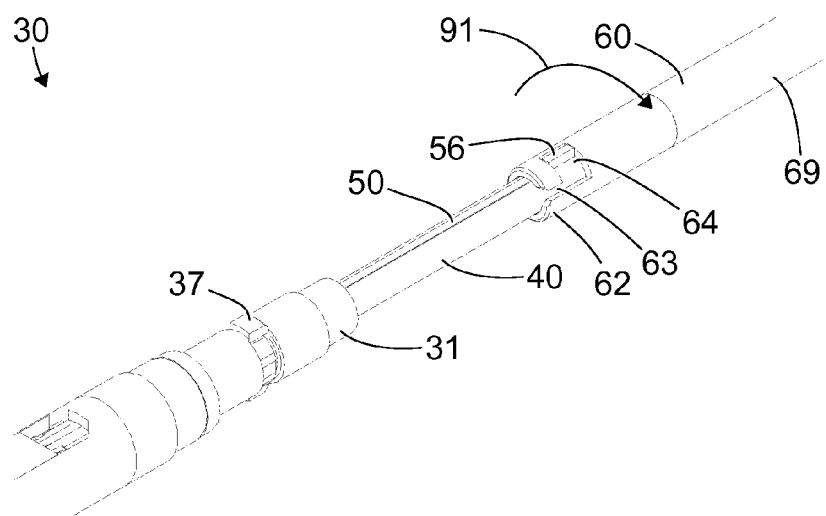
FIG. 7 shows a further schematic axonometric view of the devices from FIGS. 5 and 6.

FIG. 7 shows a further axonometric view of the grasping device from FIG. 5 and of the cutting device 50 from FIG. 6. In the view in FIG. 7, the cutting device 50 is arranged in the groove 45 in the transmission rod 40 (cf. FIG. 5). The distal end 52 of the cutting device 50 (cf. FIG. 6) is arranged here in the grasping device and in particular between the jaw parts 32, 34. The projection 56 protrudes from the groove 45.

FIG. 7 also shows the internal inner shaft 60, which has substantially a tubular shape or the shape of a jacket of a circular cylinder. At its distal end 62, the internal inner shaft 60 has an L-shaped slit with an axial or axially extending section 63 and a circumferential or circumferentially extending section 64. The width of the axial section 63 of the L-shaped slit, measured in the circumferential direction, and the width of the circumferential section 64 of the L-shaped slit, measured in the axial direction, are adapted to the dimensions of the projection 56 on the cutting device 50.

After the transmission rod 40 has been inserted into the internal inner shaft 60, the projection 56 can be guided by a relative movement in the axial direction through the axial section 63 and into the circumferential section 64. When the projection 56 on the cutting device 50 is located in the circumferential section 64 of the L-shaped slit at the distal end 62 of the internal inner shaft 60, the internal inner shaft 60 can be rotated relative to the grasping device 30, the transmission rod 40 and the cutting device 50, in a first direction 91, as far as the configuration shown in FIG. 7.

In the relative positioning of cutting device 50 and internal inner shaft 60 shown in FIG. 7, the cutting device 50 and the internal inner shaft 60 are rigidly coupled to each other in terms of axial movements (except for play). An axial movement of the internal inner shaft 60 is therefore associated with a corresponding axial movement of the cutting device 50. Thus, by means of the internal inner shaft 60, a movement of the cutting edge 53 at the distal end 52 of the cutting device 50 (cf. FIG. 6) can be effected in said channel (not shown in the figures) between the jaw parts 32, 34, such that, for example, tissue that is grasped by the jaw parts 32, 34 can be separated after electro-cauterization.

The internal inner shaft 60 has an insulating jacket 69, which has a distal edge lying near the L-shaped slit 63, 64, and which can extend to near the proximal end of the internal inner shaft 60.

Figure 8:
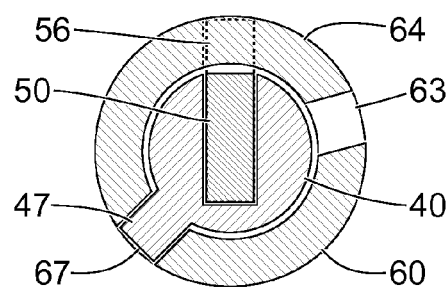
FIG. 8 shows a schematic sectional view of a transmission device and of an inner shaft.

FIG. 8 shows a schematic sectional view of an example of how the mechanical coupling, explained above with reference to FIG. 7, between the projection 56 at the proximal end of the cutting device 50 and the L-shaped slit 63, 64 at the distal end 62 of the internal inner shaft 60 is locked. The sectional plane in FIG. 8 is perpendicular to the plane of the drawing of FIG. 1, perpendicular to the plane of the drawing of FIG. 2, parallel to the plane of the drawing of FIG. 3, and perpendicular to the plane of the drawing of FIG. 4. The sectional plane in FIG. 8 lies immediately proximally of the distal end 62 of the internal inner shaft 60 in the area of the axial section 63 of the L-shaped slit (cf. FIGS. 4 and 7).

The internal inner shaft 60 has an axial, or axially extending, locking slit 67 which lies substantially opposite the L-shaped slit 63, 64. Thus, in relation to the views shown in FIGS. 5 and 7, the axial locking slit 67 lies on a side facing away from the viewer. The transmission rod 40 has a projection 47, which corresponds to the axial locking slit 67 on the internal inner shaft 60 and which, for example, is in the form of a lug, an axially extending web or a pin.

The angle position of the projection 47 relative to the groove 45 (cf. FIGS. 4 and 7) in the transmission rod 40 and the angle position of the axial locking slit 67 relative to the L-shaped slit 63, 64 in the internal inner shaft 60 are chosen such that the projection 56 on the cutting device 50, arranged in the groove 45 in the transmission rod 40, is held in the circumferential section 64 of the L-shaped slit at the distal end 62 of the internal inner shaft 60 when the projection 47 on the transmission rod 40 engages in the axial locking slit 67 on the internal inner shaft 60, as is shown in FIG. 8. The projection 47 is arranged so far distally of the proximal end of the groove 45 in the transmission rod 40 (cf. FIGS. 5 and 7) that, first of all, the cutting device 50 can be inserted into the groove 45 in the transmission rod 40 and can be coupled to the distal end 62 of the internal inner shaft 60 in the manner described above with reference to FIG. 7. Thereafter, the internal inner shaft 60 is moved distally together with the cutting device 50. It is only with this movement of the internal inner shaft 60 in the distal direction that the projection 47 on the transmission rod 40 engages in the axial locking slit 67 on the internal inner shaft 60, as is shown in FIG. 8, in order to lock the mechanical connection between the cutting device 50 and the internal inner shaft 60.

Figure 9:
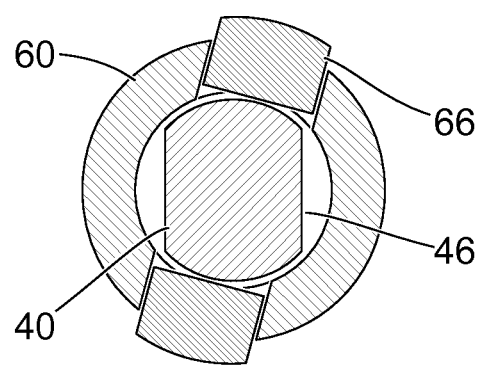
FIG. 9 shows a schematic sectional view of a further transmission device and of an inner shaft.

FIG. 9 shows a schematic sectional view of another example of how the internal inner shaft 60 is locked relative to the transmission rod 40. The sectional plane in FIG. 9 is perpendicular to the plane of the drawing of FIG. 1, perpendicular to the plane of the drawing of FIG. 2, parallel to the plane of the drawing of FIG. 3, perpendicular to the plane of the drawing of FIG. 4, and parallel to the sectional plane in FIG. 8.

The transmission rod 40 has two flat surfaces 46 lying opposite each other. The internal inner shaft 60 has two openings lying opposite each other, in which a bolt 66 is in each case mounted so as to be radially movable. The bolts 66 are in particular movable between radially inward locking positions and the radially outward unlocking positions shown in FIG. 9. The bolts 66 can be held in the recesses in the internal inner shaft 60 by an O-ring made of an elastic material or by other devices not shown in FIG. 9 and/or can be pressed radially inward into the locking positions.

Figure 10:
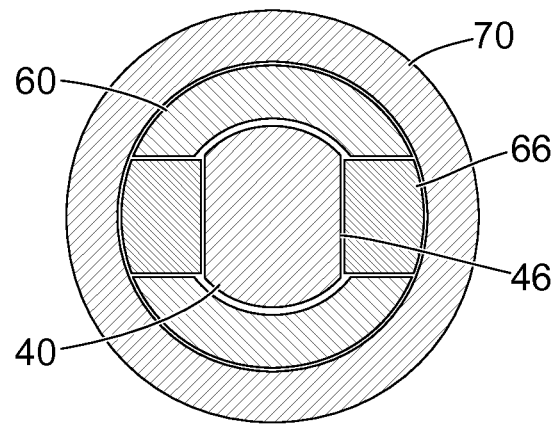
FIG. 10 shows a further schematic sectional view of the transmission device and of the inner shaft from FIG. 9.

FIG. 10 shows a further schematic sectional view of the example from FIG. 9. The sectional plane in FIG. 10 corresponds to the sectional plane in FIG. 9. The view in FIG. 10 differs from the view in FIG. 9 in that the internal inner shaft 60 is rotated relative to the transmission rod 40 to the extent that the bolts 66 can assume their radially inward locking positions and in so doing can bear on the flat surfaces 46 on the transmission rod 40.

In the view in FIG. 10, the transmission rod 40 and the internal inner shaft 60 are arranged in the external inner shaft 70. Here, radially outer surfaces of the bolts 66 bear on the inner surface of the external inner shaft 70. In this way, the bolts 66 are held with a form fit in their locking position shown in FIG. 10. Thus, when the transmission rod 40 and the internal inner shaft 60 are arranged in the external inner shaft 70 as shown in FIG. 10, the transmission rod 40 is locked in terms of rotation about its longitudinal axis relative to the internal inner shaft 60.

The angle positions of the flat surfaces 46 relative to the groove 45 in the transmission rod 40 (cf. FIGS. 5 and 7) and the angle positions of the openings in the internal inner shaft 60, receiving the bolts 66, relative to the L-shaped slit 63, 64 at the distal end 62 of the internal inner shaft 60 are chosen such that, in the locked configuration shown in FIG. 10, the projection 56 of the cutting device 50 is held in the groove 45 in the form-fit connection shown in FIG. 7 with the circumferential section 64 of the L-shaped slit at the distal end 62 of the internal inner shaft 60. Thus, in the configuration shown in FIG. 10, the mechanical connection between cutting device 50 and inner shaft 60 is locked.

The locking between transmission rod 40 and internal inner shaft 60, as has been explained with reference to FIGS. 9 and 10, can be arranged near the distal end of the internal inner shaft 60 or, if the transmission rod 40 and the internal inner shaft 60 have a sufficiently torsionally rigid design, can be arranged at any other desired location as far as the proximal ends of the transmission rod 40 and of the internal inner shaft 60.

| Reference signs | |
|---|---|
| 10 | medical instrument |
| 11 | proximal end of the medical instrument 10 |
| 12 | distal end of the medical instrument 10 |
| 18 | manipulation device at the proximal end 11 of the medical instrument 10 |
| 20 | outer shaft of the medical instrument 10 |
| 21 | proximal end of the outer shaft 20 |
| 22 | distal end of the outer shaft 20 |
| 23 | tubular section of the outer shaft 20 |
| 24 | pivot joint at the distal end 22 of the outer shaft 20 |
| 25 | pivot axis of the pivot joint 24 |
| 27 | L-shaped groove at the distal end 22 of the outer shaft 20 |
| 28 | rotation axis of the pivot joint 24 |
| 30 | grasping device at the distal end 12 of the medical instrument 10 |
| 31 | proximal end of the grasping device 30 |
| 32 | stationary jaw part of the grasping device 30 |
| 34 | pivotable jaw part of the grasping device 30 |
| 35 | pivot axis of the pivotable jaw part 34 |
| 37 | catch at the proximal end 31 of the grasping device 30 |
| 38 | longitudinal axis of the grasping device 30 |
| 40 | transmission rod of the medical instrument 10 |
| 41 | proximal end of the transmission rod 40 |
| 45 | groove in the transmission rod 40 |
| 46 | flattened surface on the transmission rod 40 |
| 47 | projection on the transmission rod 40 |
| 50 | cutting device at the distal end 12 of the medical instrument 10 |
| 51 | proximal end of the cutting device 50 |
| 52 | distal end of the cutting device 50 |
| 53 | cutting edge on the cutting device 50 |
| 54 | rod-shaped area of the cutting device 50 |
| 56 | projection at the proximal end 51 of the cutting device 50 |
| 60 | internal inner shaft of the medical instrument 10 |
| 61 | proximal end of the internal inner shaft 60 |
| 62 | distal end of the internal inner shaft 60 |
| 63 | axial section of an L-shaped slit at the distal end 62 |
| 64 | circumferential section of an L-shaped slit at the distal end 62 |
| 66 | bolt on the internal inner shaft 60 |
| 67 | axial locking slit on the internal inner shaft 60 |
| 69 | insulating jacket on the internal inner shaft 60 |
| 70 | external inner shaft of the medical instrument 10 |
| 71 | proximal end of the external inner shaft 70 |

The invention claimed is:

1. A medical instrument, comprising:
an outer shaft having a proximal end, a distal end, a pivot joint between the proximal end and the distal end, and a rotation joint between the pivot joint and the proximal end;
a manipulation device at the proximal end of the outer shaft;
a tool at the distal end of the outer shaft having a first effecting device and a second effecting device;
a first transmission device to transmit an axial force to control the first effecting device and a rotational torque to control the first effecting device and the second effecting device;
a second transmission device to transmit an axial force to control the second effecting device;
a third transmission device to control the pivot joint and the rotation joint.

2. The medical instrument according to claim 1, wherein the tool and the outer shaft have coupling devices configured to effect a releasable mechanical connection of the tool to the distal end of the outer shaft.

3. The medical instrument according to claim 1, in wherein the outer shaft and the manipulation device have coupling devices configured to effect a releasable mechanical connection of the proximal end of the outer shaft to the manipulation device.

4. The medical instrument according to claim 1, wherein the first transmission device and the second transmission device are arranged coaxially in the outer shaft.

5. The medical instrument according to claim 1, wherein the first transmission device and the second transmission device are arranged alongside each other in the outer shaft.

6. The medical instrument according to claim 1, in which the first effecting device is designed as a bipolar electrosurgical instrument with mutually electrically insulated electrodes, wherein one of the mutually electrically insulated electrodes is connected electrically conductively to the outer shaft and another of the mutually electrically insulated electrodes is connected electrically conductively to the first transmission device.

7. The medical instrument according to claim 1, wherein the rotation joint is arranged proximally of the tool and is configured to rotate the tool relative to the outer shaft.

8. The medical instrument according to claim 1, wherein the first effecting device comprises at least two jaw parts, at least one of the at least two jaw parts being pivotal, configured to grasp or squeeze tissue.

9. The medical instrument according to claim 1, wherein the second effecting device comprises a cutting device configured to cut through tissue.

10. The medical instrument according to claim 9, wherein the first transmission device comprises a transmission rod with a longitudinal groove, wherein the cutting device is disposed at least partially in the groove.

11. The medical instrument according to claim 1, wherein the first effecting device and the second effecting device operate independently of one another.

12. The medical instrument according to claim 1, further comprising a locking device provided on the second transmission device configured to couple the second transmission device to the first transmission device, in such a way that the second transmission device is rotatably fixed relative to the first transmission device.

13. The medical instrument according to claim 12, wherein the second transmission device is mechanically connected to the tool in a releasable manner by a bayonet coupling.

14. The medical instrument of claim 1, wherein the outer shaft, first transmission device, second transmission device, and third transmission device are curvable.

15. The medical instrument of claim 1, wherein the third transmission device is arranged coaxially in the outer shaft.

16. The medical instrument of claim 1, wherein the rotation joint is disposed a maximum distance away from the pivot joint being equal to about 10 times the diameter of the outer shaft.

17. A medical instrument, comprising:
a curvable outer shaft having a pivot joint;
a manipulation device at a proximal end of the outer shaft;
a tool at a distal end of the outer shaft, with a first effecting device for a first function and a second effecting device for a second function;
a first transmission device in the outer shaft configured to transmit an axial force to control the first effecting device and a rotational torque to control the first effecting device and the second effecting device;

a second transmission device in the outer shaft configured to transmit an axial force to control the second effecting device;
a third transmission device, of which the distal end is coupled to the pivot joint, and which controls the pivot joint;
a rotation joint arranged proximally of the pivot joint, configured to rotate the pivot joint relative to the proximal end of the outer shaft;
wherein the first transmission device and the second transmission device are each designed to be flexible with respect to bending at least in sections;
wherein a first portion of the outer shaft is curved independently of a second portion of the outer shaft;
wherein the third transmission device is further designed to control the rotation joint.

18. The medical instrument according to claim 17, wherein the third transmission device is arranged coaxially in the outer shaft.

19. The medical instrument according to claim 17, wherein the rotation joint is disposed a maximum distance away from the pivot joint being equal to about 10 times the diameter of the outer shaft.

* * * * *